(12) United States Patent
Sadanand

(10) Patent No.: US 9,037,211 B1
(45) Date of Patent: May 19, 2015

(54) BLADDER MONITORING DEVICE

(71) Applicant: Siddharth Sadanand, Toronto (CA)

(72) Inventor: Siddharth Sadanand, Toronto (CA)

( * ) Notice: Subject to any disclaimer, the term of this patent is extended or adjusted under 35 U.S.C. 154(b) by 91 days.

(21) Appl. No.: 13/713,841

(22) Filed: Dec. 13, 2012

Related U.S. Application Data

(60) Provisional application No. 61/576,750, filed on Dec. 16, 2011.

(51) Int. Cl.
*A61B 5/0492* (2006.01)
*A61B 5/0488* (2006.01)
*A61B 5/00* (2006.01)

(52) U.S. Cl.
CPC ............ *A61B 5/04882* (2013.01); *A61B 5/0488* (2013.01); *A61B 5/0492* (2013.01); *A61B 5/6852* (2013.01); *A61B 5/6853* (2013.01); *A61B 5/6874* (2013.01)

(58) Field of Classification Search
CPC ............. A61B 5/04882; A61B 5/0492; A61B 5/6853; A61B 5/6874
USPC .................................................. 600/373, 546
See application file for complete search history.

(56) References Cited

U.S. PATENT DOCUMENTS

| | | | | |
|---|---|---|---|---|
| 4,063,548 | A * | 12/1977 | Klatt et al. ..................... | 600/546 |
| 5,085,218 | A * | 2/1992 | Heil et al. ...................... | 600/373 |
| 5,154,177 | A * | 10/1992 | Eisman et al. ................ | 600/373 |
| 5,649,976 | A * | 7/1997 | Malewicz ...................... | 607/138 |
| 5,662,699 | A * | 9/1997 | Hamedi et al. ................ | 607/138 |
| 7,079,882 | B1 * | 7/2006 | Schmidt ........................ | 600/373 |
| 7,338,480 | B2 * | 3/2008 | Nakajima et al. ............. | 604/509 |
| 8,688,237 | B2 * | 4/2014 | Stanislaus et al. ............ | 607/124 |
| 2008/0255441 | A1* | 10/2008 | Hadani .......................... | 600/373 |
| 2011/0046432 | A1* | 2/2011 | Simon et al. .................... | 600/14 |
| 2012/0179063 | A1* | 7/2012 | Bharucha et al. ............. | 600/561 |

* cited by examiner

*Primary Examiner* — Lee S Cohen
(74) *Attorney, Agent, or Firm* — Blakely Sokoloff Taylor & Zafman LLP

(57) ABSTRACT

A device, kit and method for monitoring muscle activity. The device may include an electrode having an annular profile substantially similar to that of the muscle. During a monitoring operation, the electrode contacts a substantial portion of the muscle and detects the muscle activity. In some cases, the electrode may be positioned around a catheter device to facilitate advancing of the electrode to the desired muscle. The catheter device may then be advanced through a lumen of the body to the muscle to be monitored. A balloon of the catheter device may be expanded once the catheter device is properly positioned to secure the electrode against the muscle.

13 Claims, 5 Drawing Sheets

BLADDER MONITORING DEVICE

CROSS-REFERENCE TO RELATED APPLICATION

The application claims the benefit of the earlier filing date of U.S. Provisional Patent Application No. 61/576,750, filed Dec. 16, 2011 and incorporated herein by reference.

BACKGROUND

1. Field

An apparatus and method for monitoring the activity of muscle tissues, in particular an electrode device for monitoring the electrical activity of muscle tissues of the bladder. Other embodiments are also described and claimed.

2. Background

Electromyography (EMG) involves testing the electrical activity of muscles. Electromyographic monitoring of muscle tissue within the lower extremities, bowel and bladder using an electromyograph is essential during most spinal cord surgeries. In particular, the electromyograph detects the electrical potential generated by muscle cells when the cells are electrically, mechanically or neurologically stimulated. Based on the activity of the muscle cells, the surgeon can determine whether the surgical operation on the spinal cord is putting the innervating nerve root itself or, in some cases, the innervated muscle at risk. In the case of intramuscular electromyographic monitoring, monitoring is done by inserting needle electrodes into specific muscle groups. Extremity muscles and even the rectal sphincter muscle can be monitored by intramuscular electromyography. For example, in the case of the rectal sphincter, monitoring can be achieved by inserting a needle percutaneously through the skin into the sphincter muscle. It is difficult, however, to monitor deeper muscle groups such as the bladder sphincter using intramuscular electromyography because it is difficult to advance a needle into this region.

BRIEF DESCRIPTION OF THE DRAWINGS

The following illustration is by way of example and not by way of limitation in the figures of the accompanying drawings in which like references indicate like elements. It should be noted that references to "an" or "one" embodiment in this disclosure are not necessarily to the same embodiment, and such references mean at least one.

DETAILED DESCRIPTION

In this section we shall explain several preferred embodiments with reference to the appended drawings. Whenever the shapes, relative positions and other aspects of the parts described in the embodiments are not clearly defined, the scope of the embodiments is not limited only to the parts shown, which are meant merely for the purpose of illustration. Also, while numerous details are set forth, it is understood that some embodiments may be practiced without these details. In other instances, well-known structures and techniques have not been shown in detail so as not to obscure the understanding of this description.

Figure 1:
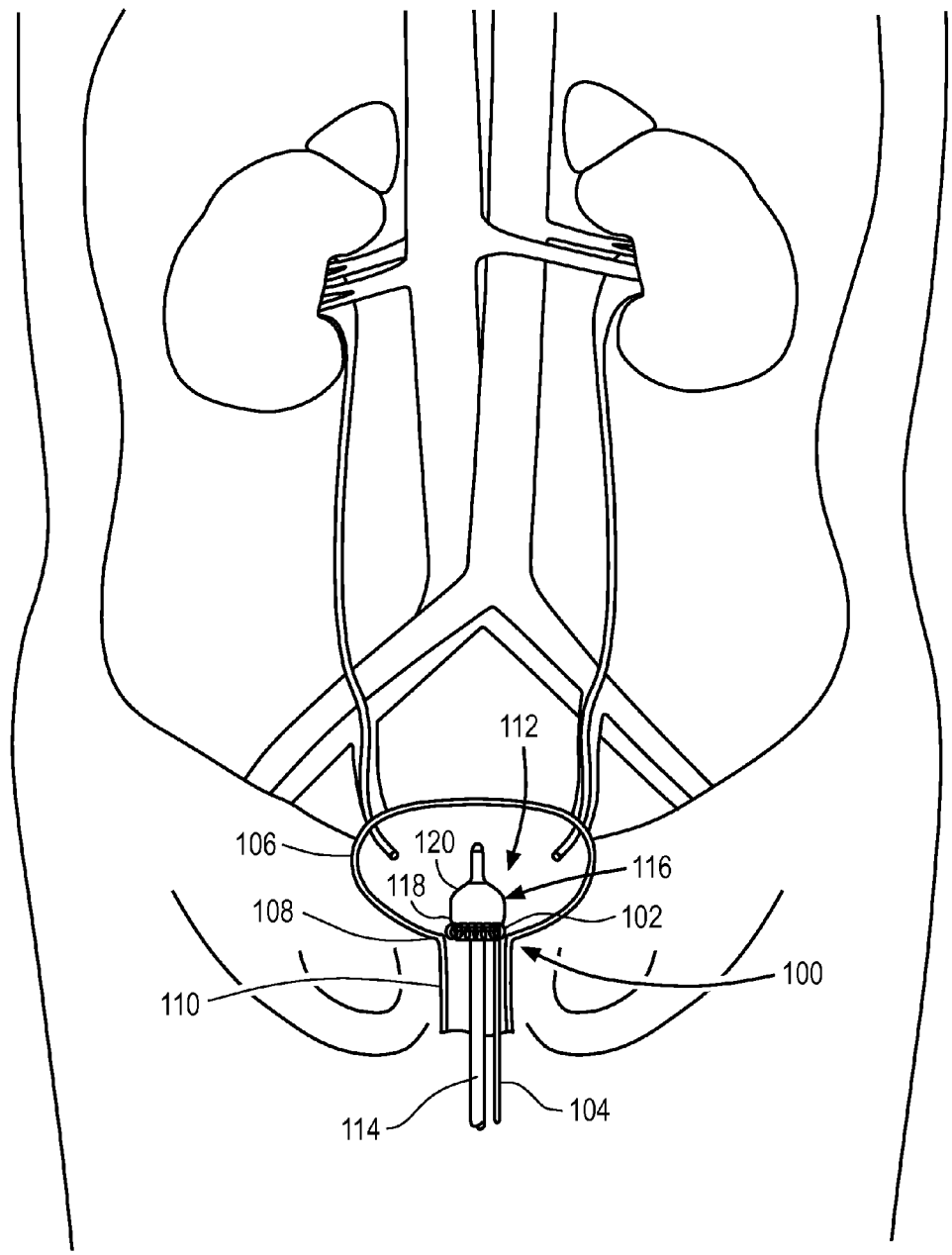
FIG. 1 illustrates a side cut out view of an embodiment of a monitoring device positioned within a bladder.

FIG. 1 illustrates a side cut out view of an embodiment of a monitoring device positioned within a bladder. As previously discussed, it is challenging to monitor the electrical activity of deep muscle groups such as the bladder sphincter during surgery using EMG because this area is difficult to reach with a needle. In particular, as can be seen from FIG. 1, bladder sphincter 108 is found between bladder 106 and urethra 110. Bladder sphincter 108 is a circular muscle that constricts the orifice between bladder 106 and urethra 110 and is therefore an important muscle group in preventing conditions such as urinary incontinence. During surgery, particularly a spinal surgery, it is important for the surgeon to be able to monitor bladder sphincter 108 to ensure they are not performing any operations that may compromise the functionality of this muscle.

Monitoring device 100 includes electrode 102 that is configured to allow for monitoring of muscle groups such as bladder sphincter 108. In particular, in one embodiment, electrode 102 may be a ring shaped electrode that can be placed within bladder 106 and contact bladder sphincter 108. In the preferred embodiment, electrode 108 is a monopolar electrode device. It is contemplated, however, that in other embodiments, electrode 108 may be a bipolar electrode device. In embodiments where electrode 102 is to be used to monitor bladder sphincter 108, electrode 102 may have a diameter substantially similar to that of bladder sphincter 108. Since electrode 102 has a similar shape as that of bladder sphincter 108, electrode 102 can contact a substantial area of bladder sphincter 108 thereby providing an accurate reading of the electrical activity of the entire muscle area. It is important that the electrode 102 contact a substantial area of bladder sphincter 108 as this results in a more accurate EMG signal.

Electrode 102 may be held against a substantial area of bladder sphincter 108 by balloon 116, which in some embodiments is a balloon of a urinary catheter. Representatively, since electrode 102 is positioned near the base of balloon 116, when balloon 116 is positioned within urethra 106 and pulled toward urethra 110, it pushes electrode 102 against bladder sphincter 108. In addition, electrode 102 may have a coiled configuration to increase the electrode's contact surface with bladder sphincter 108. For example, electrode 102 may be made of a conductive wire type material that may be coiled and connected at each end to form a coiled structure in the shape of a ring. It is noted, however, that in some embodiments the wire need not be connected at each end to maintain the ring shape. In addition, it is contemplated that electrode 102 may have a modifiable size so that it can monitor muscle groups having a variety of shapes and sizes. For example, the coiled wire forming electrode 102 may have a resiliency similar to a spring that allows it to expand or contract thereby changing or modifying a diameter of electrode 102. In this aspect, electrode 102 can be securely placed, in one instance, within a muscle group having a large diameter (e.g., larynx) and, in another instance, contracted so that it can be placed within a muscle group having a smaller diameter (e.g., bladder sphincter). The conductive material may be any type of material suitable for insertion within the body. For example, the conductive material may be a nickel alloy, titanium alloy, nickel titanium alloy, stainless steel, or other corrosion resistant alloy. Lead 104 may be connected to electrode 102 and extend out urethra 110 to a monitoring station that can analyze and display the monitoring results to the care provider.

For example, lead 104 may be an EMG lead which can transmit electrical signals detected by electrode 102 to an electromyograph.

In some embodiments, catheter device 112 may be used to advance monitoring device 100 into bladder 106 and position device 100 against bladder sphincter 108. Representatively, catheter device 112 may include cannula 114 which is dimensioned to be inserted through urethra 110 and into bladder 106. Catheter device 112 may include expandable balloon 116 having a proximal portion 118 and distal portion 120. Balloon 116 can be expanded once positioned within bladder 106 to hold catheter device 112 in place. Electrode 102 is positioned around cannula 114 next to proximal portion 118 of balloon 116. Electrode 102 may be held at this position around cannula 114 by a clip, adhesive or other similar technique suitable for securing one object to another. In other embodiments, a diameter of ring shaped electrode 102 may be substantially similar to that of cannula 114 such that electrode 102 fits snuggly around cannula 114 and is held in place by frictional forces. In still further embodiments, electrode 102 may be built into an outer surface of the wall forming cannula 114, for example molded around the outer surface. Additionally, in some embodiments, electrode 102 may be removably attached to cannula 114 so that once electrode 102 is in position, catheter device 112 may be removed from the patient and electrode 102 may remain within the patient for further monitoring. Such a configuration may be desirable, where electrode 102 is used to monitor the electrical activity of a muscle group through which it is desirable to maintain fluid flow (e.g., the esophagus, the larynx etc.).

Catheter device 112 is then inserted into urethra 110 with electrode 102 attached and advanced into bladder 106. Once balloon 116 is positioned within bladder 106, balloon 116 is expanded. Balloon 116 has a larger diameter than bladder sphincter 108 and therefore prevents catheter device 112 from being removed from bladder 106. In addition to preventing removal of catheter device 112, the expansion of balloon 116 secures electrode 102 against bladder sphincter 108. Lead 104 runs along a side of cannula 114 and out of the patient's body to a monitoring station. In some embodiments, catheter device 112 is a catheter such as a Foley catheter that is typically inserted into the bladder during surgical operations. In other embodiments, catheter device 112 may be any type of catheter configured to be inserted within the body.

Figure 2:
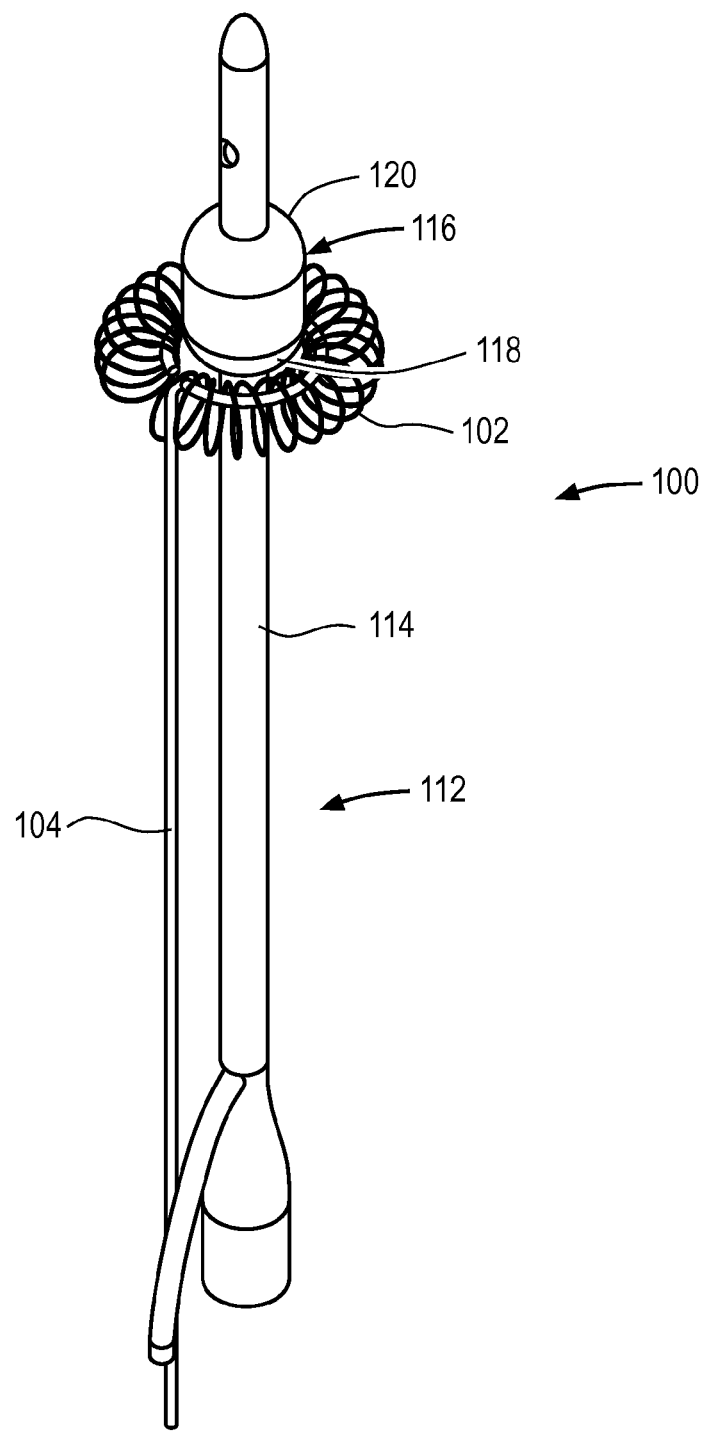
FIG. 2 illustrates a perspective view of the monitoring device of FIG. 1.

FIG. 2 illustrates a perspective view of the monitoring device of FIG. 1. FIG. 2 illustrates monitoring device 100 outside of the bladder so that the various structural components may be more clearly seen. In particular, it can be seen from this view that electrode 102 is made of a coiled wire that has a ring like shape. Lead 104 is attached to electrode 102 and transmits the electrical signals obtained by electrode 102 to a monitoring station. As previously discussed, monitoring device 100 may be positioned within the desired body area, for example the bladder sphincter, using catheter device 112. In this aspect, electrode 102 may be positioned around a portion of cannula 114 next to proximal portion 118 of balloon 116. Once catheter device 112 is advanced into bladder 106, balloon 116 is expanded to hold catheter device 112 and electrode 102 in place against bladder sphincter 108. It is contemplated, however, that in some embodiments once electrode 102 is at the desired position, balloon 116 may be contracted so that catheter device 112 can be removed while electrode 102 remains in position.

Figure 3:
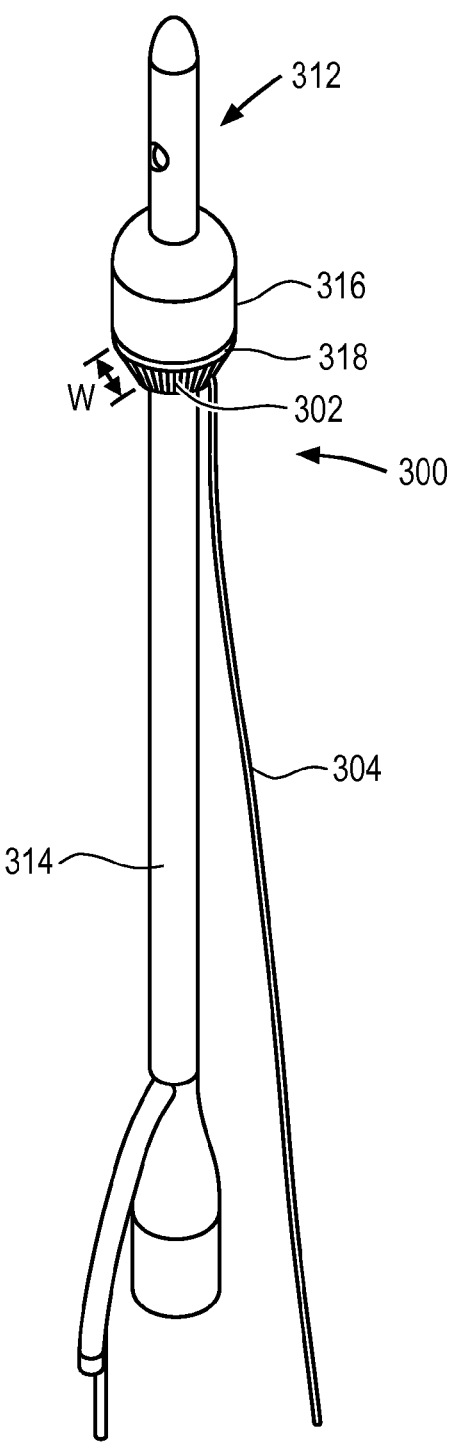
FIG. 3 illustrates a perspective view of another embodiment of a monitoring device.

In addition, although in one embodiment, electrode 102 includes a coiled, ring shaped structure, it is further contemplated that electrode 102 may have other shapes and sizes. FIG. 3 illustrates a perspective view of another embodiment of a monitoring device. In this embodiment, monitoring device 300 includes electrode 302 connected to lead 304. Similar to the electrode of FIG. 1, electrode 302 is made of a conductive material and has a ring like configuration, however, in this embodiment, a surface area of electrode 302 is increased by expanding a width (w) of electrode 302 instead of using the coil configuration. In particular, electrode 302 is formed by a thin plate of conductive material having a width (w). The width (w) may be any width suitable to increase a contact area between electrode 302 and the orifice within which it is positioned. For example, in some embodiments electrode 302 may have a width substantially similar to a width of proximal portion 318 of balloon 316 and a funnel like shape that conforms to the surface of balloon 316 such that balloon 316 essentially wedges electrode 302 within the desired orifice. It is further noted that electrode 302 may form a complete ring, a partial ring or may be made of segments that are mounted around catheter device 312.

Figure 4:
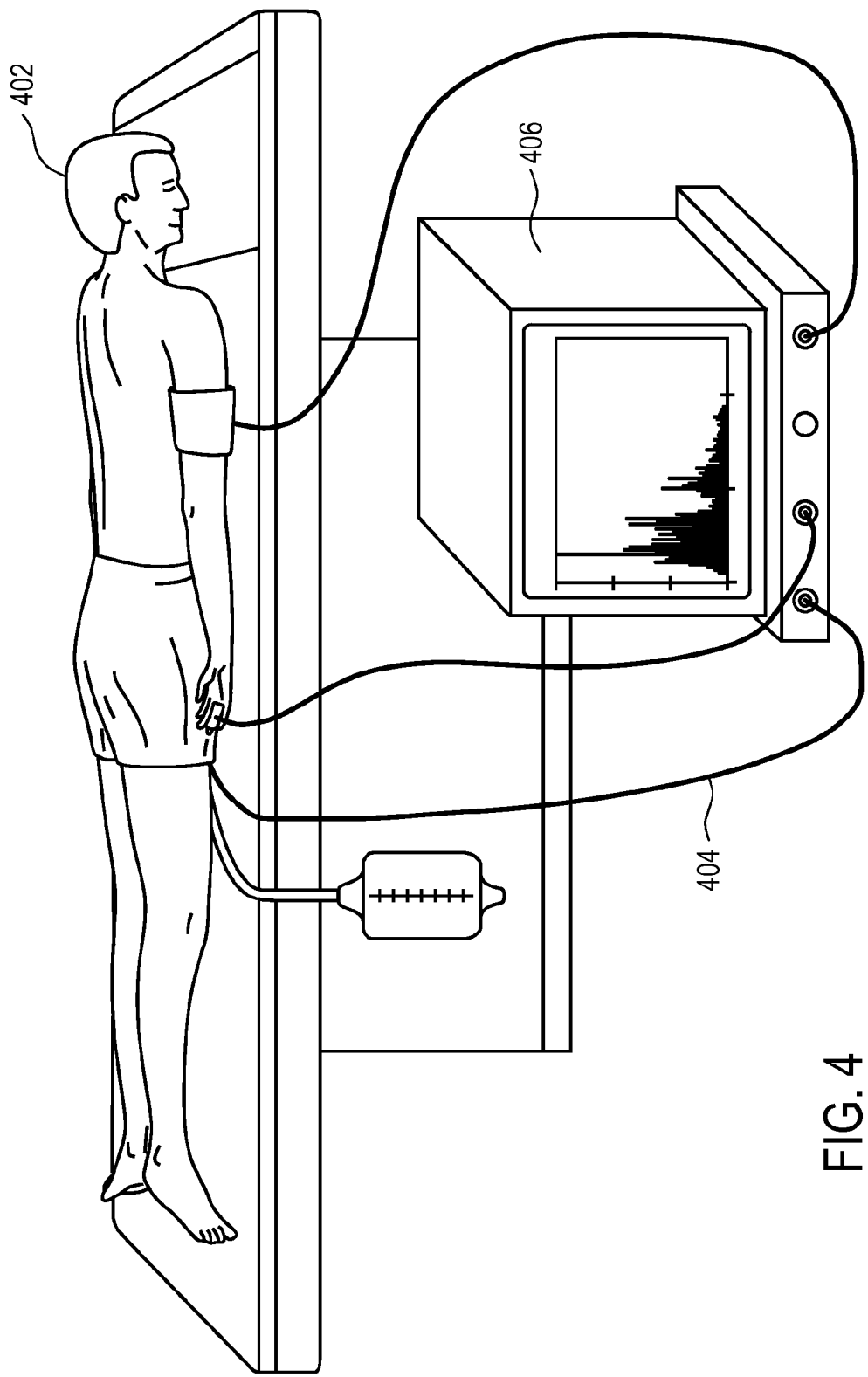
FIG. 4 illustrates the use of a monitoring device on a patient.

FIG. 4 illustrates the use of a monitoring device on a patient. The electrode of any of the previously discussed monitoring devices, for example monitoring device 100 or monitoring device 300, is inserted into the bladder of patient 402 using any of the previously discussed catheter devices. Lead 402 of the monitoring device, which extends out of patient 402 and is connected to a monitoring station such as electronic device 406, communicates signals from the electrode to electronic device 406. Electronic device 406 in some cases may be an electromyograph capable of receiving signals (e.g., muscle membrane potential electrical signals) from the electrode and analyzing the signals to detect muscle activation levels. Electronic device 406 may, in some cases, process and display the results on a display screen interface to the health care provider. The health care provider can then review the display and monitor the electrical activity of the muscle tissues being monitored to ensure they are not putting any of the muscle tissues at risk throughout the surgical procedure.

Figure 5:
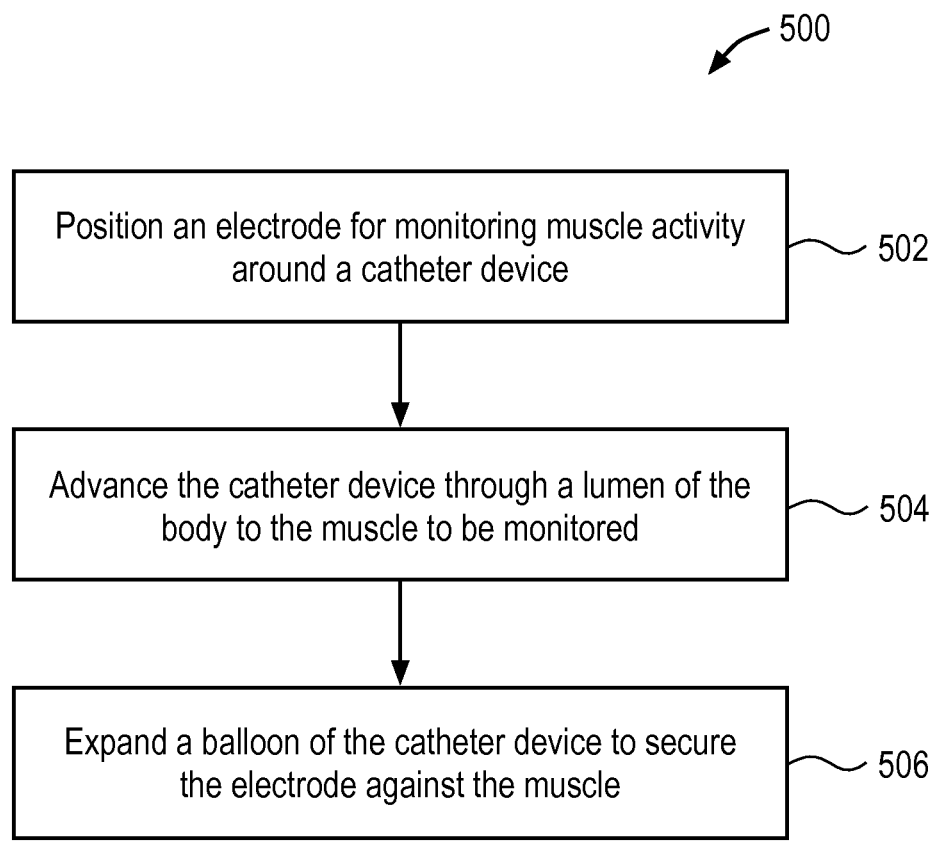
FIG. 5 illustrates a flow chart of one embodiment of a method for monitoring using the monitoring device.

FIG. 5 illustrates one embodiment of a process for monitoring muscle activity using any of the previously discussed monitoring devices. Representatively, in one embodiment the monitoring process 500 includes positioning an electrode for monitoring muscle activity around a catheter device (block 502). The electrode may be positioned around the catheter device prior to insertion within the patient by, for example, inserting the electrode around a free end of the catheter device cannula and advancing the electrode to a base of a balloon attached to the cannula. Alternatively, in some embodiments, the electrode may be separated along its annulus to form a gap in the ring and the cannula inserted through the gap. Once the electrode is positioned around the catheter, the catheter device can be advanced through a lumen of the body to the muscle to be monitored (block 504). Representatively, in the case of monitoring a bladder sphincter muscle, the catheter may be inserted through the urethra and into the bladder such that the balloon is positioned within the bladder while a portion of the cannula extends outside of the body to allow for inflation of the balloon. Once in position, the balloon can be expanded to secure the electrode against the muscle (block 506). In particular, since the electrode is positioned at the base of the balloon (portion of the balloon connected to the cannula), when the balloon is expanded the electrode is held affixed between the balloon and the bladder sphincter muscle.

In the preceding detailed description, specific embodiments are described. It will, however, be evident that various modifications and changes may be made thereto without departing from the broader spirit and scope of the claims. For example, although an electrode having a ring shaped configuration for monitoring a bladder sphincter is described, it is further contemplated that the electrode may have any size and shape suitable for monitoring an electrical activity of any muscle tissue within a body cavity that is difficult to monitor. Representatively, the electrode may be configured to monitor muscle cells within the throat such as the larynx, esophagus, stomach, intestines, or rectum. For example, the electrode may be attached to an end of a cannula suitable for advancing through a body lumen connecting to the larynx, esophagus, stomach, intestines or rectum. The cannula can then be advanced through the lumen to the desired muscle group such that the electrode is positioned on or within the muscle group and can monitor the muscle activity. The specification and drawings are, accordingly, to be regarded in an illustrative rather than restrictive sense.

The invention claimed is:

1. An apparatus for monitoring muscle activity comprising:
   an electrode for monitoring muscle activity, the electrode having a profile substantially similar to that of the muscle such that the electrode is capable of contacting a substantial portion of the muscle and monitoring the muscle activity, and wherein the electrode comprises a funnel shape; and
   a cannula coupled to a proximal end of a balloon, wherein the electrode encircles the cannula near the proximal end of the balloon such that during a monitoring operation, the electrode is positioned between the balloon and the muscle and the electrode is wedged within an opening of the muscle during the monitoring operation.

2. The apparatus of claim 1 further comprising:
   a lead wire operable to electrically couple the electrode to an electromyograph to facilitate monitoring of the muscle activity.

3. The apparatus of claim 1 wherein the electrode is molded to one of the cannula or the balloon.

4. The apparatus of claim 1 wherein the funnel shape is formed by a conductive material that contacts the muscle during the monitoring operation.

5. The apparatus of claim 1 wherein the muscle is the bladder sphincter muscle.

6. A kit for monitoring muscle activity comprising:
   an electrode for monitoring an activity of a muscle, the electrode being formed by a self-expanding coiled wire having a profile substantially similar to that of the muscle such that a substantial portion of the coiled wire contacts the muscle; and
   a catheter dimensioned for insertion and positioning of the electrode at the muscle, the catheter having a balloon and wherein the self-expanding coiled wire is positioned around a proximal end of the balloon and is modifiable, in response to a size of the muscle, between an expanded configuration and a contracted configuration to accommodate the size of the muscle.

7. The kit of claim 6 wherein the electrode is removably attached to the catheter.

8. The kit of claim 6 wherein the electrode is fixedly attached to the catheter.

9. The kit of claim 6 wherein the catheter comprises a cannula coupled to the proximal end of the balloon, wherein the electrode encircles the cannula near the proximal end of the balloon such that during a monitoring operation, the electrode is positioned between the balloon and the muscle.

10. The kit of claim 6 wherein the electrode comprises a conductive material that encircles the catheter and contacts the muscle during a monitoring operation.

11. The kit of claim 6 wherein the electrode comprises an outer surface that is wedged within, and in contact with, an opening of the muscle during a monitoring operation.

12. A method for monitoring muscle activity comprising:
    positioning an electrode for monitoring muscle activity around a catheter device, wherein the catheter device comprises a cannula and a balloon, and the electrode comprises a funnel shape such that positioning comprises inserting the electrode over an end of the cannula and advancing the electrode to the balloon;
    advancing the catheter device and the electrode through a lumen of a body and a circular muscle to be monitored; and
    expanding the balloon of the catheter device along one side of the circular muscle to secure the electrode between the balloon and the one side of the circular muscle.

13. The method of claim 12 wherein the lumen is a portion of a urethra of the body and the muscle is a bladder sphincter muscle.

* * * * *